US010899862B2

(12) United States Patent
Benz et al.

(10) Patent No.: US 10,899,862 B2
(45) Date of Patent: *Jan. 26, 2021

(54) HYDROPHOBIC INTRAOCULAR LENS

(71) Applicant: Benz Research and Development Corp., Sarasota, FL (US)

(72) Inventors: Patrick H. Benz, Sarasota, FL (US); Adam Reboul, Sarasota, FL (US)

(73) Assignee: BENZ RESEARCH AND DEVELOPMENT CORP., Sarasota, FL (US)

( * ) Notice: Subject to any disclaimer, the term of this patent is extended or adjusted under 35 U.S.C. 154(b) by 101 days.

This patent is subject to a terminal disclaimer.

(21) Appl. No.: 16/047,823

(22) Filed: Jul. 27, 2018

(65) Prior Publication Data
US 2018/0334520 A1    Nov. 22, 2018

Related U.S. Application Data

(63) Continuation of application No. 15/481,791, filed on Apr. 7, 2017, now Pat. No. 10,196,470.

(60) Provisional application No. 62/337,318, filed on May 16, 2016.

(51) Int. Cl.
| C08F 220/68 | (2006.01) |
| B29D 11/02 | (2006.01) |
| A61F 2/16 | (2006.01) |
| A61L 27/16 | (2006.01) |
| C08L 27/10 | (2006.01) |
| C08L 29/02 | (2006.01) |

(52) U.S. Cl.
CPC .............. *C08F 220/68* (2013.01); *A61F 2/16* (2013.01); *A61L 27/16* (2013.01); *B29D 11/023* (2013.01); *C08L 27/10* (2013.01); *C08L 29/02* (2013.01); *A61F 2210/0095* (2013.01); *A61L 2430/16* (2013.01)

(58) Field of Classification Search
CPC ........ C08F 220/68; C08F 2/50; C08F 220/22; C08F 220/30; C08F 220/56; C08F 2810/20; B29D 11/023; A61F 2/16; A61F 2210/0095; A61F 2250/0056; A61L 27/16; A61L 2430/16; A61L 27/50; C08L 27/10; C08L 29/02; C08L 33/08; C08L 33/14; C08L 33/26
See application file for complete search history.

(56) References Cited

U.S. PATENT DOCUMENTS

| 5,326,506 A | 7/1994 | Vanderbilt |
| 5,693,095 A | 12/1997 | Freeman et al. |
| 6,267,784 B1 | 7/2001 | Benz et al. |
| 6,281,319 B1 | 8/2001 | Mentak |
| 6,365,652 B2 | 4/2002 | Gupta et al. |
| 6,517,750 B2 | 2/2003 | Benz et al. |
| 6,635,731 B2 | 10/2003 | Mentak |
| 6,635,732 B2 | 10/2003 | Mentak |
| 7,067,602 B2 | 6/2006 | Benz et al. |
| 7,083,645 B2 | 8/2006 | Mentak |
| 7,387,642 B2 | 6/2008 | Benz et al. |
| 7,947,796 B2 | 5/2011 | Benz et al. |
| 8,247,511 B2 | 8/2012 | Mentak |
| 9,561,302 B2 | 2/2017 | Benz et al. |
| 2002/0027302 A1 | 3/2002 | Benz et al. |
| 2002/0058723 A1 | 5/2002 | Benz et al. |
| 2002/0058724 A1 | 5/2002 | Benz et al. |
| 2005/0131183 A1 | 6/2005 | Benz et al. |
| 2006/0199929 A1 | 9/2006 | Benz et al. |
| 2006/0276606 A1 | 12/2006 | Benz et al. |
| 2008/0221235 A1 | 9/2008 | Benz et al. |
| 2013/0253159 A1 | 9/2013 | Benz et al. |

FOREIGN PATENT DOCUMENTS

| EP | 0 441 383 A2 | 8/1991 |
| WO | WO-96/40303 A1 | 12/1996 |
| WO | WO-00/79312 A1 | 12/2000 |
| WO | WO-01/18079 A1 | 3/2001 |
| WO | WO-2010/128266 A1 | 11/2010 |
| WO | WO-2013/040434 A1 | 3/2013 |
| WO | WO-2015/161199 A1 | 10/2015 |

OTHER PUBLICATIONS

Garcia, F. et al. "Reaction Kinetics and Gel Effect on the Polymerization of 2-Ethoxyethyl Methacrylate and 2(2-Ethoxyethoxy) Ethyl Methacrylate." Journal of Polymer Science: Part A: Polymer Chemistry, vol. 40, 2002, pp. 3987-4001.
International Search Report and Written Opinion dated Aug. 14, 2017 in PCT/US2017/032698 (13 pgs.).

*Primary Examiner* — Jessica M Roswell
(74) *Attorney, Agent, or Firm* — Foley & Lardner LLP

(57) ABSTRACT

A hydrophobic intraocular lens (IOL) with excellent non-glistening characteristics, high Abbe number, excellent mechanical properties comprising at least one copolymer comprising: (a) a first monomeric subunit comprising a polymerized (meth)acrylate group and at least one alkoxy-alkoxyalkyl side group, (b) a second monomeric subunit different from the first monomeric subunit comprising a polymerized (meth)acrylate group, at least one side group comprising (i) an aryloxy moiety with at least one halogen, and (ii) an aliphatic carbon moiety linking the aryloxy moiety with the polymerized (meth)acrylate group, wherein the aliphatic carbon moiety comprises at least one hydroxyl substituent.

15 Claims, No Drawings

HYDROPHOBIC INTRAOCULAR LENS

RELATED APPLICATIONS

This application is a continuation of U.S. application Ser. No. 15/481,791, filed Apr. 7, 2017; which claims priority to U.S. Provisional Appl. No. 62/337,318 filed May 16, 2016; the complete disclosures of both of which are hereby incorporated by reference in their entirety.

BACKGROUND

Various types of intraocular lenses (IOLs) are known. For example, there are known one-piece intraocular lenses and composite intraocular lens having multiple pieces. A one-piece intraocular lens is one where both optic and non-optic portions are made from one material. The non-optic portions of IOLs are referred to as haptic portions, and are used for attachment purposes.

Both hydrophobic and hydrophilic foldable IOLs are described in the prior art in, for example, U.S. Pat. Nos. 7,947,796, 7,387,642, 7,067,602, 6,517,750 and 6,267,784 each of which is hereby incorporated by reference in its entirety. See also, for example, U.S. Patent Publication Nos. 2013/0253159, 2008/0221235, 2006/0276606, 2006/0199929, 2005/0131183, 2002/0058724, 2002/0058723 and 2002/0027302, along with WO/2015/161199, each of which is hereby incorporated by reference in its entirety.

Additionally, lens materials comprising the monomer 2-hydroxy-3-phenoxypropyl acrylate are disclosed in the prior art in, for example, WO 2010/128266, WO 2001/018079, WO 2000/079312, WO 96/40303, and U.S. Pat. No. 5,693,095. The lens material 2-ethoxyethyl methacrylate is also known in the art as a compound with a low glass transition temperature. See, for example, Garcia, F., et al., *J. of Polymer Science: Part A: Polymer Chemistry*, Vol. 40, 3987-4001 (2002).

A need exists, however, for improved IOL materials including hydrophobic materials, which do not, e.g., suffer from excessive glistening, can provide an absence of stickiness characteristics after injection of the IOL, and can provide for difficult-to-achieve combinations of properties, such as good injectability while maintaining good mechanical properties and more accurately replicating a human lens.

SUMMARY

Embodiments described herein include, for example, copolymers, lenses, intraocular lenses, blanks for intraocular lenses, and methods for making and methods of using compositions and intraocular lenses.

One embodiment provides, for example, an intraocular lens comprising at least one copolymer comprising: (a) a first monomeric subunit comprising a polymerized (meth)acrylate group and at least one alkoxyalkoxyalkyl side group, (b) a second monomeric subunit different from the first monomeric subunit comprising a polymerized (meth)acrylate group, at least one side group comprising (i) an aryloxy moiety comprising at least one halogen, and (ii) an aliphatic carbon moiety linking the aryloxy moiety with the polymerized (meth)acrylate group, wherein the aliphatic carbon moiety comprises at least one hydroxyl substituent, (c) a third monomeric subunit different from the first and second monomeric subunits comprising a polymerized (meth)acrylate group, at least one side group comprising (i) an aryloxy moiety, and (ii) an aliphatic carbon moiety linking the aryloxy moiety with the polymerized (meth) acrylate group, wherein the aliphatic carbon moiety comprises at least one hydroxyl substituent, (d) optionally a fourth monomeric subunit different from the first, second, and third monomeric subunits comprising a polymerized acrylate or (meth)acrylate group, and at least one alkylene oxide side group, and (e) optionally a fifth monomeric subunit different from the first, second, third, and fourth monomeric subunits comprising a polymerized (meth)acrylate group and at least one alkoxyalkyl side group.

Provided herein is a composition comprising at least one copolymer comprising: (a) a first monomeric subunit comprising a polymerized (meth)acrylate group and at least one alkoxyalkoxyalkyl side group, (b) a second monomeric subunit different from the first monomeric subunit comprising a polymerized (meth)acrylate group, at least one side group comprising (i) an aryloxy moiety comprising at least one halogen, and (ii) an aliphatic carbon moiety linking the aryloxy moiety with the polymerized (meth)acrylate group, wherein the aliphatic carbon moiety comprises at least one hydroxyl substituent, (c) a third monomeric subunit different from the first and second monomeric subunits comprising a polymerized (meth)acrylate group, at least one side group comprising (i) an aryloxy moiety, and (ii) an aliphatic carbon moiety linking the aryloxy moiety with the polymerized (meth)acrylate group, wherein the aliphatic carbon moiety comprises at least one hydroxyl substituent, (d) optionally a fourth monomeric subunit different from the first, second, and third monomeric subunits comprising a polymerized acrylate or (meth)acrylate group, and at least one alkylene oxide side group, and (e) optionally a fifth monomeric subunit different from the first, second, third, and fourth monomeric subunits comprising a polymerized (meth)acrylate group and at least one alkoxyalkyl side group.

Also provided is a method for making a composition comprising at least one copolymer comprising monomeric subunits comprising: preparing a co-monomer mixture comprising: (a) a first monomeric subunit comprising a polymerized (meth)acrylate group and at least one alkoxyalkoxyalkyl side group, (b) a second monomeric subunit different from the first monomeric subunit comprising a polymerized (meth)acrylate group, at least one side group comprising (i) an aryloxy moiety comprising at least one halogen, and (ii) an aliphatic carbon moiety linking the aryloxy moiety with the polymerized (meth)acrylate group, wherein the aliphatic carbon moiety comprises at least one hydroxyl substituent, (c) a third monomeric subunit different from the first and second monomeric subunits comprising a polymerized (meth)acrylate group, at least one side group comprising (i) an aryloxy moiety, and (ii) an aliphatic carbon moiety linking the aryloxy moiety with the polymerized (meth) acrylate group, wherein the aliphatic carbon moiety comprises at least one hydroxyl substituent, (d) optionally a fourth monomeric subunit different from the first, second, and third monomeric subunits comprising a polymerized acrylate or (meth)acrylate group, and at least one alkylene oxide side group, and (e) optionally a fifth monomeric subunit different from the first, second, third, and fourth monomeric subunits comprising a polymerized (meth)acrylate group and at least one alkoxyalkyl side group; polymerizing the co-monomer mixture by adding a photo or thermal initiator.

Also provided is an intraocular lens comprising at least one copolymer consisting essentially of: (a) a first monomeric subunit comprising a polymerized (meth)acrylate group and at least one alkoxyalkoxyalkyl side group, (b) a second monomeric subunit different from the first monomeric subunit comprising a polymerized (meth)acrylate group, at least one side group comprising (i) an aryloxy moiety comprising at least one halogen, and (ii) an aliphatic carbon moiety linking the aryloxy moiety with the polymerized (meth)acrylate group, wherein the aliphatic carbon moiety comprises at least one hydroxyl substituent, (c) a third monomeric subunit different from the first and second monomeric subunits comprising a polymerized (meth)acrylate group, at least one side group comprising (i) an aryloxy moiety, and (ii) an aliphatic carbon moiety linking the aryloxy moiety with the polymerized (meth)acrylate group, wherein the aliphatic carbon moiety comprises at least one hydroxyl substituent, and (d) optionally a fourth monomeric subunit different from the first, second, and third monomeric subunits comprising a polymerized acrylate or (meth)acrylate group, and at least one alkylene oxide side group and (e) optionally a fifth monomeric subunit different from the first, second, third, and fourth monomeric subunits comprising a polymerized (meth)acrylate group and at least one alkoxyalkyl side group.

Further provided herein is a composition comprising a co-monomer mixture comprising: (a) a first monomeric subunit comprising a polymerized (meth)acrylate group and at least one alkoxyalkoxyalkyl side group, (b) a second monomeric subunit different from the first monomeric subunit comprising a polymerized (meth)acrylate group, at least one side group comprising (i) an aryloxy moiety comprising at least one halogen, and (ii) an aliphatic carbon moiety linking the aryloxy moiety with the polymerized (meth) acrylate group, wherein the aliphatic carbon moiety comprises at least one hydroxyl substituent, (c) a third monomeric subunit different from the first and second monomeric subunits comprising a polymerized (meth)acrylate group, at least one side group comprising (i) an aryloxy moiety, and (ii) an aliphatic carbon moiety linking the aryloxy moiety with the polymerized (meth)acrylate group, wherein the aliphatic carbon moiety comprises at least one hydroxyl substituent, (d) optionally a fourth monomeric subunit different from the first, second, and third monomeric subunits comprising a polymerized acrylate or (meth)acrylate group, and at least one alkylene oxide side group, and (e) optionally a fifth monomeric subunit different from the first, second, third, and fourth monomeric subunits comprising a polymerized (meth)acrylate group and at least one alkoxyalkyl side group.

At least one advantage for at least one embodiment includes excellent non-glistening properties for an IOL, particularly for a hydrophobic IOL.

At least one additional advantage for at least one embodiment includes good unfolding properties for an IOL. For example, an IOL embodied herein may unfold in five to ten seconds.

At least one additional advantage for at least one embodiment includes an absence of stickiness characteristics after injection of the IOL (e.g., the haptic does not stick to the optic).

At least one additional advantage for at least one embodiment includes a refractive index of greater than 1.50 in combination with low glistening as measured by Trattler severity index.

Yet another advantage for at least one embodiment is a high diopter IOL able to pass through a small orifice injector, such as a 1.8 mm injector, e.g., a Medicel Viscoject™ 1.8 mm.

Yet another advantage for at least one embodiment is an IOL with a low glass transition temperature (e.g., less than 12° C.) that maintains a high refractive index (e.g., higher than 1.51).

Yet another advantage for at least one embodiment is an IOL with an Abbe value of 45 or higher.

DETAILED DESCRIPTION

Introduction

All references cited herein are incorporated by reference in their entirety.

Intraocular lens are generally known in the art. See, for example, U.S. Pat. Nos. 7,947,796; 7,387,642; 7,067,602; 6,517,750; and 6,267,784.

As used herein, the term "(meth)acrylate" refers to acrylic or methacrylic acid, esters of acrylic or methacrylic acid, and salts, amides, and other suitable derivatives of acrylic or methacrylic acid, and mixtures thereof. Illustrative examples of suitable (meth)acrylic monomers include, without limitation, the following methacrylate esters: methyl methacrylate, ethyl methacrylate, n-propyl methacrylate, n-butyl methacrylate (BMA), isopropyl methacrylate, isobutyl methacrylate, n-amyl methacrylate, n-hexyl methacrylate, isoamyl methacrylate, 2-hydroxyethyl methacrylate, 2-hydroxypropyl methacrylate, N,N-dimethylaminoethyl methacrylate, N,N-diethylaminoethyl methacrylate, t-butylaminoethyl methacrylate, 2-sulfoethyl methacrylate, trifluoroethyl methacrylate, glycidyl methacrylate (GMA), benzyl methacrylate, allyl methacrylate, 2-n-butoxyethyl methacrylate, 2-chloroethyl methacrylate, sec-butyl-methacrylate, tert-butyl methacrylate, 2-ethylbutyl methacrylate, cinnamyl methacrylate, crotyl methacrylate, cyclohexyl methacrylate, cyclopentyl methacrylate, 2-ethoxyethyl methacrylate, furfuryl methacrylate, hexafluoroisopropyl methacrylate, methallyl methacrylate, 3-methoxybutyl methacrylate, 2-methoxybutyl methacrylate, 2-nitro-2-methylpropyl methacrylate, n-octylmethacrylate, 2-ethylhexyl methacrylate, 2-phenoxyethyl methacrylate, 2-phenylethyl methacrylate, phenyl methacrylate, propargyl methacrylate, tetrahydrofurfuryl methacrylate and tetrahydropyranyl methacrylate. Example of suitable acrylate esters include, without limitation, methyl acrylate, ethyl acrylate, n-propyl acrylate, isopropyl acrylate, n-butyl acrylate (BA), n-decyl acrylate, isobutyl acrylate, n-amyl acrylate, n-hexyl acrylate, isoamyl acrylate, 2-hydroxyethyl acrylate, 2-hydroxypropyl acrylate, N,N-dimethylaminoethyl acrylate, N,N-diethylaminoethyl acrylate, t-butylaminoethyl acrylate, 2-sulfoethyl acrylate, trifluoroethyl acrylate, glycidyl acrylate, benzyl acrylate, allyl acrylate, 2-n-butoxyethyl acrylate, 2-chloroethyl acrylate, sec-butyl-acrylate, tert-butyl acrylate, 2-ethylbutyl acrylate, cinnamyl acrylate, crotyl acrylate, cyclohexyl acrylate, cyclopentyl acrylate, 2-ethoxyethyl acrylate, furfuryl acrylate, hexafluoroisopropyl acrylate, methallyl acrylate, 3-methoxybutyl acrylate, 2-methoxybutyl acrylate, 2-nitro-2-methylpropyl acrylate, n-octylacrylate, 2-ethylhexyl acrylate, 2-phenoxyethyl acrylate, 2-phenylethyl acrylate, phenyl acrylate, propargyl acrylate, tetrahydrofurfuryl acrylate and tetrahydropyranyl acrylate.

One embodiment provides an intraocular lens comprising at least one copolymer comprising a series of monomeric subunits including, for example:

(a) a first monomeric subunit comprising a polymerized (meth)acrylate group and at least one alkoxyalkoxyalkyl side group, (b) a second monomeric subunit different from the first monomeric subunit comprising a polymerized (meth)acrylate group, at least one side group comprising (i) an aryloxy moiety comprising at least one halogen, and
(ii) an aliphatic carbon moiety linking the aryloxy moiety with the polymerized (meth)acrylate group, wherein the aliphatic carbon moiety comprises at least one hydroxyl substituent, (c) a third monomeric subunit different from the first and second monomeric subunits comprising a polymerized (meth)acrylate group, at least one side group comprising
(i) an aryloxy moiety, and
(ii) an aliphatic carbon moiety linking the aryloxy moiety with the polymerized (meth)acrylate group, wherein the aliphatic carbon moiety comprises at least one hydroxyl substituent, (d) optionally a fourth monomeric subunit different from the first, second, and third monomeric subunits comprising a polymerized acrylate or (meth)acrylate group, and at least one polyalkylene oxide side group, and (e) optionally a fifth monomeric subunit different from the first, second, third, and fourth monomeric subunits comprising a polymerized (meth)acrylate group and at least one alkoxyalkyl side group First/Primary Monomeric Subunit The first monomeric subunit can be the monomer subunit present in the largest amount as measured by weight percent for the copolymer. The first monomeric subunit comprises a polymerizable moiety, such as acrylate, methacrylate, acrylamide and/or methacrylamide. The first monomeric subunit also comprises at least one alkoxyalkoxyalkyl side group. The first monomeric subunit may include hydrophobic monomeric subunits that are suitable for foldable IOLs. Examples include but are not limited to alkoxyalkoxyalkyl (meth)acrylates or alkoxyalkoxy (meth)acrylamides.

In another embodiment, the first monomeric subunit comprising a polymerized acrylate or methacrylate group may instead comprise a polymerized acrylamide or methacrylamide group that is optionally substituted at the nitrogen by hydrogen or a $C_1$ to $C_5$ alkyl. In some embodiments, the first monomer subunit comprises a polymerized methacrylate group.

Alkoxyalkoxyalkyl methacrylate monomeric subunits can be represented by the formula $R_{15}$—O—$R_5$—O—$R_6$-MA where $R_5$, $R_6$, $R_{15}$ are alkyl groups and "MA" is methacrylate. Alkoxyalkoxyalkyl acrylate monomeric subunits can be represented by the formula $R_{20}$—O—$R_7$—O—$R_8$-A where $R_7$, $R_8$, $R_{20}$ are alkyl groups and "A" is acrylate. Both alkoxyalkoxyalkyl methacrylates and alkoxyalkoxyalkyl acrylates are ester-containing monomer compounds as will be recognized by those skilled in the art. In some embodiments, $R_5$ to $R_8$, $R_{15}$, and $R_{20}$ can be independently selected from alkyl groups having 1 to 5 carbon atoms and in some embodiments 1, 2, 3, 4, or 5 carbon atoms. With respect to $R_6$, it will be understood that the alkyl group is bonded to the O of the $R_5$—O group and is also bonded to the O atom of the MA group. Similarly, with respect to $R_8$, it will be understood that the alkyl group is bonded to the O of the $R_7$—O group and is also bonded to the O atom of the A group. Alkyl groups that may be used in accordance with the embodiments herein include straight chain alkyl groups, including but not limited to methyl, ethyl, propyl, butyl, and pentyl groups. Alkyl groups may also include branched chain isomers of straight chain alkyl groups including, but not limited to, the following, which are provided by way of example only: —CH($CH_3$)$_2$, —CH($CH_3$)($CH_2CH_3$), —CH($CH_2CH_3$)$_2$, —C($CH_3$)$_3$, and the like. In some embodiments, the alkoxyalkoxyalkyl methacrylate or alkoxyalkoxyalkyl acrylate is selected where $R_5$, to $R_8$, $R_{15}$, and $R_{20}$ have 1, 2, 3, or 4 carbon atoms. Examples of some specific alkoxyalkoxyalkyl methacrylate and alkoxyalkoxyalkyl acrylate monomer subunits useful for forming the copolymers of the embodiments herein include, but are not limited to, methoxymethoxyethyl methacrylate, ethoxyethoxyethyl methacrylate, propoxypropoxyethyl methacrylate, butoxybutoxymethyl methacrylate, methoxymethoxypropyl methacrylate, ethoxyethoxypropyl methacrylate, propoxypropoxypropyl methacrylate, butoxybutoxypropyl methacrylate, methoxymethoxybutyl methacrylate, ethoxyethoxybutyl methacrylate, propoxypropoxybutyl methacrylate, butoxybutoxybutyl methacrylate, methoxymethoxyethyl acrylate, ethoxyethoxyethyl acrylate, propoxypropoxyethyl acrylate, butoxybutoxymethyl acrylate, methoxymethoxypropyl acrylate, ethoxyethoxypropyl acrylate, propoxypropoxypropyl acrylate, butoxybutoxypropyl acrylate, methoxymethoxybutyl acrylate, ethoxyethoxybutyl acrylate, propoxypropoxybutyl acrylate, and butoxybutoxybutyl acrylate. In some preferred embodiments, the copolymer includes ethoxyethoxyethyl methacrylate (EOEOEMA).

Hence, a particularly preferred embodiment provides an intraocular lens, wherein the alkoxyalkoxyalkyl group is a $C_3$ to $C_{12}$ group. In one embodiment, the alkoxyalkoxyalkyl group comprises two oxygen atoms. In a specific embodiment, the alkoxyalkoxyalkyl group is 2-ethoxyethoxyethyl.

Second Monomeric Subunit

The second monomeric subunit can be the monomer subunit present in the second largest amount as measured by weight percent for the copolymer. This subunit comprises a polymerizable moiety, such as acrylate, methacrylate, acrylamide and/or methacrylamide. The subunit also comprises an aliphatic spacer comprising one or more hydroxyl moieties. Finally, the second monomeric subunit comprises an optionally substituted aryl or aryloxy moiety comprising at least one halogen, including, for example, F, Cl, Br, and/or I. In another embodiment, the second monomeric subunit comprising a polymerized acrylate or methacrylate group may instead comprise a polymerized acrylamide or methacrylamide group that is optionally substituted at the nitrogen by hydrogen or a $C_1$ to $C_5$ alkyl. In some embodiments, the second monomer subunit comprises a polymerized methacrylate group.

For example, aryloxyalkyl methacrylate monomeric subunits can be represented by the formula Ar—O—$R_1$-MA where Ar is an optionally substituted aryl compound such as, for example, an optionally substituted phenyl, $R_1$ is an aliphatic spacer such as a bivalent alkyl group and "MA" is methacrylate. Alternatively, aryloxyalkyl acrylate monomeric subunits can be represented by the formula Ar—O—$R_2$-A where Ar is an optionally substituted aryl compound such as, for example an optionally substituted phenyl, $R_2$ is an aliphatic spacer such as a bivalent alkyl group and "A" is acrylate. Likewise, aryloxyalkyl acrylamide monomeric subunits can be represented by the formula Ar—O—$R_3$-AA where Ar is an optionally substituted aryl compound such as, for example, an optionally substituted phenyl, $R_3$ is an aliphatic spacer such as a bivalent alkyl group and "AA" is acrylamide. In addition, aryloxyalkyl methacrylamide monomeric subunits can be represented by the formula Ar—O—$R_4$-MAA where Ar is an optionally substituted aryl compound such as, for example, an optionally substituted phenyl, $R_4$ is an aliphatic spacer such as a bivalent alkyl group and "MAA" is methacrylamide. The bivalent group $R_1$, $R_2$, $R_3$, and $R_4$ may be further substituted by at least one hydroxy group. The AA or MAA monomeric subunits can be optionally substituted at the nitrogen by hydrogen or a $C_1$ to $C_5$ alkyl. Examples of $C_1$ to $C_5$ alkyl include methyl, ethyl, propyl, butyl, pentyl, and isomers thereof.

Both hydroxy and halogen-substituted aryloxyalkyl methacrylates and hydroxy and halogen-substituted aryloxyalkyl acrylates are ester-containing monomer compounds as will be recognized by those skilled in the art. Likewise, those skilled in the art would recognize hydroxy and halogen-substituted aryloxyalky acrylamides and hydroxy and halogen-substituted aryloxyalky methacrylamides as amide-containing monomer compounds.

In some embodiments, $R_1$, $R_2$, $R_3$, and $R_4$ can be independently selected from hydroxy-substituted alkyl groups having 1 to 5 carbon atoms and in some embodiments 1, 2, 3, 4, or 5 carbon atoms, the alkyl group is substituted by one or more hydroxy groups. With respect to $R_1$, it will be understood that the hydroxy-substituted alkyl group is bonded to the O of the Ar—O group and is also bonded to the O atom of the MA group. Similarly, with respect to $R_2$, it will be understood that the hydroxy-substituted alkyl group is bonded to the O of the Ar—O group and is also bonded to the O atom of the A group. Similarly, with respect to $R_3$, it will be understood that the hydroxy-substituted alkyl group is bonded to the O of the Ar—O group and is also bonded to the N atom of the AA group. Similarly, with respect to $R_4$, it will be understood that the hydroxy-substituted alkyl group is bonded to the O of the Ar—O group and is also bonded to the N atom of the MAA group. The hydroxy group may be substituted to any carbon of the alkyl group. Hydroxy-substituted alkyl groups that may be used in accordance with the embodiments herein include straight chain alkyl groups, including but not limited to methyl, ethyl, propyl, butyl, and pentyl groups, wherein at least one C—H is substituted for C—OH. Alkyl groups may also include branched chain isomers of straight chain alkyl groups including, but not limited to, the following, which are provided by way of example only: —CH(CH$_3$)$_2$, —CH(CH$_3$)(CH$_2$CH$_3$), —CH(CH$_2$CH$_3$)$_2$, —C(CH$_3$)$_3$, and the like, wherein at least one C—H is substituted for C—OH. In some embodiments, the hydroxy-substituted aryloxyalkyl methacrylate or hydroxy-substituted aryloxyalkyl acrylate is selected where $R_1$ and $R_2$ have 1, 2, 3, or 4 carbon atoms.

Specific embodiments of $R_1$, $R_2$, $R_3$, and $R_4$ are by way of non-limiting example and the like. The AA or MAA monomeric subunits may be optionally substituted at the nitrogen by hydrogen or a $C_1$ to $C_5$ alkyl.

Aryloxy groups will be recognized by those skilled in the art to include an aryl compound bonded to an oxygen atom. In some embodiments, the aryl group comprises optionally substituted phenyl or naphthyl. In some embodiments, the aryl group may comprise one or more heteroatoms, such as by way of non-limiting example nitrogen or sulfur. The aryl moiety may be optionally substituted by one or more alkyl groups including but not limited to methyl, ethyl, propyl, butyl, and pentyl groups. The alkyl groups may be branched chain isomers of straight chain alkyl groups. The aryl moiety may be optionally substituted by one or more alkoxy groups comprising an alkyl group bound to an oxygen, the alkyl group comprising, but not limited to methyl, ethyl, propyl, butyl, and/or pentyl groups. The alkyl groups may be branched chain isomers of straight chain alkyl groups. Additionally the aryl moiety is substituted by one or more halogen groups, for example, F, Cl, Br, and/or I. In some embodiments, the aryl moiety is substituted by one halogen. In some embodiments, the aryl moiety is substituted by two, three, four, or five halogens. In some embodiments, wherein the aryl moiety is substituted by at least two halogens, the halogens can be the same or different.

Examples of some specific hydroxy and halogen-substituted aryloxyalkyl methacrylate, hydroxy and halogen-substituted aryloxyalkyl acrylate, hydroxy and halogen-substituted aryloxyalkyl methacrylamide and hydroxy and halogen-substituted aryloxyalkyl acrylamide monomeric subunits useful for forming the copolymers, but are not limited to, 2-bromo-2-hydroxy-3-phenoxypropyl acrylate, 3-bromo-2-hydroxy-3-phenoxypropyl acrylate, 4-bromo-2-hydroxy-3-phenoxypropyl acrylate, 2-bromo-2-hydroxy-3-phenoxypropyl methacrylate, 3-bromo-2-hydroxy-3-phenoxypropyl methacrylate, 4-bromo-2-hydroxy-3-phenoxypropyl methacrylate, 2-bromo-2-hydroxy-3-phenoxypropyl acrylamide, 3-bromo-2-hydroxy-3-phenoxypropyl acrylamide, 4-bromo-2-hydroxy-3-phenoxypropyl acrylamide, and/or 2-bromo-2-hydroxy-3-phenoxypropyl methacrylamide, 3-bromo-2-hydroxy-3-phenoxypropyl methacrylamide, or 4-bromo-2-hydroxy-3-phenoxypropyl methacrylamide. In some embodiments, the second monomer comprises bromo-2-hydroxy-3-phenoxypropyl methacrylate (BrHPPMA).

In some embodiments, the present copolymers may also include a second monomer that is represented by the general formula (II), wherein R' is hydrogen or methyl, Y is O or —NR'', X is H, Cl, Br, —CH$_3$, or —OCH$_3$, n is 1 to 6, m is 1 to 6, R'' is hydrogen or a $C_1$ to $C_5$ alkyl; and Z is H, OH or a halogen group.

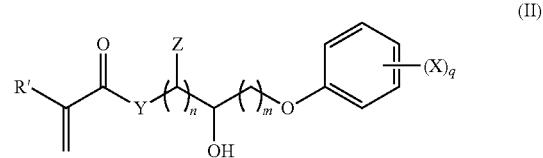

(II)

In other embodiments, n and m are 1 or 2 and X is Br, Z is H, and Y is O, and q is 1, 2, 3, 4, or 5. In some embodiments, q is 1 or 2.

Hence, one preferred embodiment provides an intraocular lens, wherein the second monomer subunit comprises a polymerized (meth)acrylate group. In another embodiment, the aryloxy group comprises a phenoxy group. In yet another embodiment, the aryloxy group comprises an unsubstituted phenoxy group. In another embodiment, the aliphatic carbon moiety of the second monomer is substituted with one hydroxyl group. In another embodiment, the aliphatic carbon moiety of the second monomer is a $C_3$ moiety. In another embodiment, the aliphatic carbon moiety of the second monomer is represented by —CH(Br)—CHOH—CH$_2$—. Finally, the side group of the second monomer, in one embodiment, comprises —CH(Br)—CHOH—CH$_2$—OPh, wherein OPh is an unsubstituted phenoxy group.

Third Monomeric Subunit

The third monomeric subunit comprises a polymerizable moiety, such as acrylate, methacrylate, acrylamide and/or methacrylamide. The subunit also comprises an aliphatic spacer comprising one or more hydroxyl moieties. Finally, the third monomeric subunit comprises an optionally substituted aryl or aryloxy moiety. In another embodiment, the third monomeric subunit comprising a polymerized acrylate or methacrylate group may instead comprise a polymerized acrylamide or methacrylamide group that is optionally substituted at the nitrogen by hydrogen or a $C_1$ to $C_5$ alkyl. In some embodiments, the third monomer subunit comprises a polymerized methacrylate group.

For example, aryloxyalkyl methacrylate monomeric subunits can be represented by the formula Ar—O—$R_1$-MA where Ar is an optionally substituted aryl compound such as, for example, an optionally substituted phenyl, $R_1$ is an aliphatic spacer such as a bivalent alkyl group and "MA" is methacrylate. Alternatively, aryloxyalkyl acrylate monomeric subunits can be represented by the formula Ar—O—$R_2$-A where Ar is an optionally substituted aryl compound such as, for example an optionally substituted phenyl, $R_2$ is an aliphatic spacer such as a bivalent alkyl group and "A" is acrylate. Likewise, aryloxyalkyl acrylamide monomeric subunits can be represented by the formula Ar—O—$R_3$-AA where Ar is an optionally substituted aryl compound such as, for example, an optionally substituted phenyl, $R_3$ is an aliphatic spacer such as a bivalent alkyl group and "AA" is acrylamide. In addition, aryloxyalkyl methacrylamide monomeric subunits can be represented by the formula Ar—O—$R_4$-MAA where Ar is an optionally substituted aryl compound such as, for example, an optionally substituted phenyl, $R_4$ is an aliphatic spacer such as a bivalent alkyl group and "MAA" is methacrylamide. The bivalent group $R_1$, $R_2$, $R_3$, and $R_4$ may be further substituted by at least one hydroxy group. The AA or MAA monomeric subunits can be optionally substituted at the nitrogen by hydrogen or a $C_1$ to $C_5$ alkyl. Examples of C1 to C5 alkyl include methyl, ethyl, propyl, butyl, pentyl, and isomers thereof.

Both hydroxy-substituted aryloxyalkyl methacrylates and hydroxy-substituted aryloxyalkyl acrylates are ester-containing monomer compounds as will be recognized by those skilled in the art. Likewise, those skilled in the art would recognize hydroxy-substituted aryloxyalky acrylamides and hydroxy-substituted aryloxyalky methacrylamides as amide-containing monomer compounds. In some embodiments, $R_1$, $R_2$, $R_3$, and $R_4$ can be independently selected from hydroxy-substituted alkyl groups having 1 to 5 carbon atoms and in some embodiments 1, 2, 3, 4, or 5 carbon atoms, the alkyl group is substituted by one or more hydroxy groups. With respect to $R_1$, it will be understood that the hydroxy-substituted alkyl group is bonded to the O of the Ar—O group and is also bonded to the O atom of the MA group. Similarly, with respect to $R_2$, it will be understood that the hydroxy-substituted alkyl group is bonded to the O of the Ar—O group and is also bonded to the O atom of the A group. Similarly, with respect to $R_3$, it will be understood that the hydroxy-substituted alkyl group is bonded to the O of the Ar—O group and is also bonded to the N atom of the AA group. Similarly, with respect to $R_4$, it will be understood that the hydroxy-substituted alkyl group is bonded to the O of the Ar—O group and is also bonded to the N atom of the MAA group. The hydroxy group may be substituted to any carbon of the alkyl group. Hydroxy-substituted alkyl groups that may be used in accordance with the embodiments herein include straight chain alkyl groups, including but not limited to methyl, ethyl, propyl, butyl, and pentyl groups, wherein at least one C—H is substituted for C—OH. Alkyl groups may also include branched chain isomers of straight chain alkyl groups including, but not limited to, the following, which are provided by way of example only: —CH($CH_3$)$_2$, —CH($CH_3$)($CH_2CH_3$), —CH($CH_2CH_3$)$_2$, —C($CH_3$)$_3$, and the like, wherein at least one C—H is substituted for C—OH. In some embodiments, the hydroxy-substituted aryloxyalkyl methacrylate or hydroxy-substituted aryloxyalkyl acrylate is selected where $R_1$ and $R_2$ have 1, 2, 3, or 4 carbon atoms. Specific embodiments of $R_1$, $R_2$, $R_3$, and $R_4$ are by way of non-limiting example 1-hydroxy propyl, 2-hydroxy propyl, 3-hydroxy propyl, 2-hydroxy butyl, 3-hydroxy butyl, 2,3-dihydroxy butyl and the like. The AA or MAA monomeric subunits may be optionally substituted at the nitrogen by hydrogen or a $C_1$ to $C_5$ alkyl.

Aryloxy groups will be recognized by those skilled in the art to include an aryl compound bonded to an oxygen atom. In some embodiments, the aryl group comprises optionally substituted phenyl or naphthyl. In some embodiments, the aryl group may comprise one or more heteroatoms, such as by way of non-limiting example nitrogen or sulfur. The aryl moiety may be optionally substituted by one or more alkyl groups including but not limited to methyl, ethyl, propyl, butyl, and pentyl groups. The alkyl groups may be branched chain isomers of straight chain alkyl groups. The aryl moiety may be optionally substituted by one or more alkoxy groups comprising an alkyl group bound to an oxygen, the alkyl group comprising, but not limited to methyl, ethyl, propyl, butyl, and/or pentyl groups. The alkyl groups may be branched chain isomers of straight chain alkyl groups.

Examples of some specific hydroxy-substituted aryloxyalkyl methacrylate, hydroxy-substituted aryloxyalkyl acrylate, hydroxy-substituted aryloxyalkyl methacrylamide and hydroxy-substituted aryloxyalkyl acrylamide monomeric subunits useful for forming the copolymers, but are not limited to, 2-hydroxy-3-phenoxypropyl acrylate, 2-hydroxy-3-phenoxypropyl methacrylate, 2-hydroxy-3-phenoxypropyl acrylamide, and/or 2-hydroxy-3-phenoxypropyl methacrylamide. In some embodiments, the first monomer comprises 2-hydroxy-3-phenoxypropyl methacrylate (HPPMA).

In some embodiments, the present copolymers may also include a third monomer that is represented by the general formula (I), wherein R' is hydrogen or methyl, Y is O or —NR", X is H, —$CH_3$, or —$OCH_3$, n is 1 to 6, R" is hydrogen or a $C_1$ to $C_5$ alkyl.

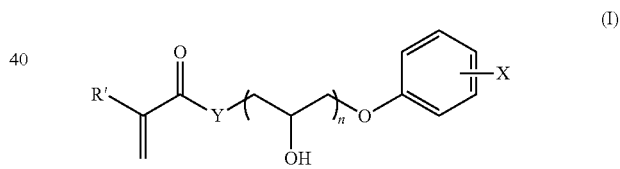

(I)

In other embodiments, n is 1 or 2 and X is hydrogen and Y is O.

Hence, one preferred embodiment provides an intraocular lens, wherein the third monomer subunit comprises a polymerized (meth)acrylate group. In another embodiment, the aryloxy group comprises a phenoxy group. In yet another embodiment, the aryloxy group comprises an unsubstituted phenoxy group. In another embodiment, the aliphatic carbon moiety of the third monomeric subunit is substituted with one hydroxyl group. In another embodiment, the aliphatic carbon moiety of the third monomeric subunit is a $C_3$ moiety. In another embodiment, the aliphatic carbon moiety of the third monomeric subunit is represented by —$CH_2$—CHOH—$CH_2$—. Finally, the side group of the third monomeric subunit, in one embodiment, comprises —$CH_2$—CHOH—$CH_2$—OPh, wherein OPh is an unsubstituted phenoxy group.

Fourth Monomeric Subunit

A fourth monomeric subunit is optional, and can be present which is different from the first, second, and third monomeric subunits. The present copolymers may also include, for example, one or more polyalkylene glycol alkylether acrylate and/or polyalkylene glycol alkylether methacrylate monomeric subunits including of higher molecular weight. Examples of polyalkylene glycol alkylether acrylate and/or polyalkylene glycol alkylether methacrylate include, for example, polyethylene glycol monomethyl ether methacrylate monomeric subunits of varying molecular weight. In some embodiments, the fifth monomer may be polyethylene glycol monomethyl ether methacrylate (200 PEG MW) or polyethylene glycol monomethyl ether methacrylate (400 PEG MW). In another embodiment, polyethylene glycol monomethyl ether methacrylate of other molecular weights may be used. Other polyethylene glycol monomethyl ether methacrylate compositions may be used.

In some embodiments, the co-polymers provided herein do not include the fourth monomeric subunit.

Hence, a particularly preferred embodiment provides an intraocular lens or IOL blank, wherein the alkyleneoxide side group is a poly(alkyleneoxide) side group. In one embodiment, the alkyleneoxide side group has a molecular weight of 100 g/mol to 2,000 g/mol. In another embodiment, the alkyleneoxide side group has a molecular weight of 100 g/mol to 1,000 g/mol. In yet another embodiment, the alkyleneoxide side group has a molecular weight of 100 g/mol to 500 g/mol. In one embodiment, the alkyleneoxide side group is a poly(ethyleneoxide) side group. In one embodiment, the fourth monomeric subunit consists of polymerized polyethylene glycol monomethyl ether methacrylate with a polyethylene glycol molecular weight of about 150 to 250. In another embodiment, the fourth monomeric subunit consists of polymerized polyethylene glycol monomethyl ether methacrylate with a polyethylene glycol molecular weight of about 350 to 450.

It is to be understood that any reference to the molecular weight of the fourth monomeric subunit refers to average molecular weight. Accordingly, 200 PEG MW refers to a polyethylene glycol monomethyl ether methacrylate that has an average molecular weight of about 200. Similarly, 400 PEG MW refers to a polyethylene glycol monomethyl ether methacrylate with an average molecular weight of about 400. 200 PEG MW and 400 PEG MW are commercially available as having an average molecular weight of about 200 or 400 respectively. In some embodiments, average molecular weight refers to a weight average molecular weight. In some embodiments, the average molecular weight is +/−5 or 10% of the value, or +/− less than 5, 10, 25, or 30 g/mol of the recited molecular weight.

Fifth Monomeric Subunit

The present copolymers may also include one or more hydrophobic monomeric subunits that can be formed from a fifth monomeric subunit different from the first, second, third, and fourth monomeric subunits. Examples of such hydrophobic monomeric subunits used to make the fifth monomeric subunits include alkoxyalkyl methacrylate and/or alkoxyalkyl acrylate monomeric subunits. In some embodiments, the fifth monomeric subunit comprises a polymerized (meth)acrylate group and containing one alkoxyalkyl side group. Alkoxyalkyl methacrylate monomeric subunits can be represented by the formula $R_5$—O—$R_6$-MA where $R_5$ and $R_6$ are alkyl groups and "MA" is methacrylate. Alkoxyalkyl acrylate monomeric subunits can be represented by the formula $R_7$—O—$R_8$-A where $R_7$ and $R_8$ are alkyl groups and "A" is acrylate. Both alkoxyalkyl methacrylates and alkoxyalkyl acrylates are ester-containing monomer compounds as will be recognized by those skilled in the art. In some embodiments, $R_5$ to $R_8$ can be independently selected from alkyl groups having 1 to 5 carbon atoms and in some embodiments 1, 2, 3, 4, or 5 carbon atoms. With respect to $R_6$, it will be understood that the alkyl group is bonded to the O of the $R_5$—O group and is also bonded to the O atom of the MA group. Similarly, with respect to $R_8$, it will be understood that the alkyl group is bonded to the O of the $R_7$—O group and is also bonded to the O atom of the A group. Alkyl groups that may be used in accordance with the embodiments herein include straight chain alkyl groups, including but not limited to methyl, ethyl, propyl, butyl, and pentyl groups. Alkyl groups may also include branched chain isomers of straight chain alkyl groups including, but not limited to, the following, which are provided by way of example only: —$CH(CH_3)_2$, —$CH(CH_3)(CH_2CH_3)$, —$CH(CH_2CH_3)_2$, —$C(CH_3)_3$, and the like. In some embodiments, the alkoxyalkyl methacrylate or alkoxyalkyl acrylate is selected where $R_5$, to $R_8$ have 1, 2, 3, or 4 carbon atoms. Examples of some specific alkoxyalkyl methacrylate and alkoxyalkyl acrylate monomeric subunits useful for forming the copolymers of the embodiments herein include, but are not limited to, methoxyethyl methacrylate, ethoxyethyl methacrylate, propoxyethyl methacrylate, butoxymethyl methacrylate, methoxypropyl methacrylate, ethoxypropyl methacrylate, propoxypropyl methacrylate, butoxypropyl methacrylate, methoxybutyl methacrylate, ethoxybutyl methacrylate, propoxybutyl methacrylate, butoxybutyl methacrylate, methoxyethyl acrylate, ethoxyethyl acrylate, propoxyethyl acrylate, butoxymethyl acrylate, methoxypropyl acrylate, ethoxypropyl acrylate, propoxypropyl acrylate, butoxypropyl acrylate, methoxybutyl acrylate, ethoxybutyl acrylate, propoxybutyl acrylate, and butoxybutyl acrylate. In some preferred embodiments, the copolymer includes ethoxyethyl methacrylate (EOEMA).

Hence, a particularly preferred embodiment provides an intraocular lens, wherein the alkoxyalkyl group is a $C_3$ to $C_{12}$ group. In one embodiment, the alkoxyalkyl group comprises a single oxygen atom. In some embodiments, the alkoxyalkyl group is not a repeating alkoxyalkyl group. In a specific embodiment, the alkoxyalkyl group is 2-ethoxyethyl.

In some embodiments, an alkoxyalkyl methacrylate and/or alkoxyalkyl acrylate monomeric subunits are utilized in the copolymer disclosed herein to produce copolymers with a higher glass transition temperature.

In some embodiments, the co-polymers provided herein do not include the fifth monomeric subunit.

Crosslinker (Sixth Monomer)

The intraocular lens can comprise a copolymer that further comprises a sixth monomeric subunit that is crosslinked. In particular, bi- or tri-functional crosslinking agents can be used to form the crosslinked subunits. However, other di- or multi-functional crosslinking agents known in the art may also be employed instead, or in addition to the bi- or tri-functional crosslinking agents.

The copolymers can be prepared using conventional polymerization techniques known to those in the field of polymer chemistry. Crosslinkers may be employed in the polymerization reaction. For example, any crosslinking or difunctional monomer, can be used in effective amounts to give the desired crosslinking density. For example, in a concentration range of 0 to about 10 percent, such as about 0.01 to about 4 percent, or in some embodiments from 0.5 to 3 percent by weight, based on the weight of the polymer.

Examples of suitable crosslinking agents include di-olefinic functional component or ethylene glycol dimethacrylate (EGDMA). Generally, crosslinkers help to enhance the resulting copolymer's dimensional stability.

In some embodiments, the compositions include one or more crosslinker with three or more polymerizable functionalities (a multi-functional crosslinking agent). An example of a multi-functional crosslinking agent includes, but is not limited to, trimethylol propane trimethacrylate (TMPTMA). The analogous acrylate crosslinking agents, for example, trimethylol propane triacrylate, may also be utilized in place of any of their methacrylate analogs or in combination with the methacrylate analogs. Some embodiments include two or more tri-functional crosslinking agents or a multi-functional crosslinking agent and a di-functional crosslinking agent known in the art or incorporated herein by reference, such as for example EGDMA. Therefore, in some embodiments, the copolymer compositions include EGDMA and/or TMPTMA. In some such embodiments, the amount of EGDMA and/or TMPTMA ranges from about 0.5 to about 5 (e.g., about 2 to about 3 or about 2.5 to about 3) percent by weight based on the weight of the dry copolymer In one embodiment, the only crosslinker used is a trifunctional crosslinker such as a trifunctional methacrylate crosslinker.

Examples of specific copolymers useful in the present embodiments are discussed in the examples where all weights are shown in grams.

Compositions/Amounts

The copolymers described herein can include the first and second monomeric subunits e.g. the alkoxyalkoxyalkyl methacrylate, alkoxyalkoxyalkyl acrylate, hydroxy and halogen-substituted aryloxyalkyl methacrylate, and hydroxy and halogen-substituted aryloxyalkyl acrylate monomeric subunits as the major components and the third and fourth monomeric subunits as the minor components, measured by weight.

Weight Amounts

In some embodiments, the copolymers provided herein may include about 30 percent to about 65 percent by weight of the first monomeric subunit based on the total weight of the copolymer. In some embodiments, the first monomeric subunit includes about 40-50 percent, about 50-60 percent, or about 50-65 percent by weight of the copolymer. In some embodiments, the first monomeric subunit includes about 40-45 percent, about 45-50 percent, about 50-55 percent, about 55-60 percent, or about 60-65 percent by weight of the copolymer. In some embodiments, the first monomeric subunit includes about 40 percent, about 41 percent, about 42 percent, about 43 percent, about 44 percent, about 45 percent, about 46 percent, about 47 percent, about 48 percent, about 49 percent, about 50 percent, about 51 percent, about 52 percent, about 53 percent, about 54 percent, about 55 percent, about 56 percent, about 57 percent, about 58 percent, about 59 percent, about 60 percent, about 61 percent, about 62 percent, about 63 percent, about 64 percent, or about 65 percent by weight of the copolymer. In some embodiments, the first monomeric subunit includes about 42.5 percent by weight of the copolymer. In some embodiments, the first monomeric subunit includes about 47.5 percent by weight of the copolymer. In some embodiments, the first monomeric subunit includes about 52.5 percent by weight of the copolymer. In some embodiments, the first monomeric subunit includes about 57.5 percent by weight of the copolymer.

In some embodiments, the first monomeric subunit may include a hydrophobic monomeric subunit. In some embodiments, the hydrophobic monomeric subunit includes EOEOEMA.

While the present claims are not limited by theory, the presence of the first monomeric subunit provides for a low glass transition temperature.

In some embodiments, the copolymers provided herein can include about 10 percent to about 30 percent by weight of the second monomeric subunit based on the total weight of the copolymer. In some embodiments, the second monomeric subunit includes about 15-25 percent by weight of the copolymer. In some embodiments, the second monomeric subunit includes about 15-20 percent, about 20-25 percent, or about 25-30 percent by weight of the copolymer. In some embodiments, the second monomeric subunit includes about 15 percent, about 16 percent, about 17 percent, about 18 percent, about 19 percent, about 20 percent, about 21 percent, about 22 percent, about 23 percent, about 24 percent, about 25 percent, about 26 percent, about 27 percent, about 28 percent, about 29 percent, or about 30 percent by weight of the copolymer. In some embodiments, the second monomeric subunit includes about 25 percent by weight of the copolymer. In some embodiments, the second monomeric subunit includes about 27.5 percent by weight of the copolymer.

In some embodiments, the second monomeric subunit includes BrHPPMA.

In the present copolymers, the total quantity of the one or more of the first and second monomeric subunits can make up the majority of the copolymer, as measured by weight. For example, in some embodiments, the total quantity of the combined amounts of any alkoxyalkoxyalkyl methacrylate, alkoxyalkoxyalkyl acrylate, hydroxy and halogen-substituted aryloxyalkyl methacrylate, and hydroxy and halogen-substituted aryloxyalkyl acrylate monomeric subunits may be about 55 percent to about 95 percent by weight based on the total weight of the copolymer. In some embodiments, the first and second monomeric subunits may include about 55-60 percent, about 55-65 percent, about 55-70 percent, about 55-75 percent, about 55-80 percent, about 55-85 percent, or about 55-90 percent by weight of the copolymer. In some embodiments, the first and second monomeric subunits may include about 55-65 percent, about 65-75 percent, about 75-85 percent, or about 75-95 percent by weight of the copolymer. In some embodiments, the first and second monomeric subunits may include about 55 percent, about 56 percent, about 57 percent, about 58 percent, about 59 percent, about 60 percent, about 61 percent, about 62 percent, about 63 percent, about 64 percent, about 65 percent, about 66 percent, about 67 percent, about 68 percent, about 69 percent, about 70 percent, about 71 percent, about 72 percent, about 73 percent, about 74 percent, about 75 percent, about 76 percent, about 77 percent, about 78 percent, about 79 percent, about 80 percent, about 81 percent, about 82 percent, about 83 percent, about 84 percent, about 85 percent, about 86 percent, about 87 percent, about 88 percent, about 89 percent, or about 90 percent, about 91 percent, about 92 percent, about 93 percent, about 94 percent, or about 95 percent by weight of the copolymer. In some embodiments, the first and second monomeric subunits may include about 72.5 percent by weight of the copolymer. In some embodiments, the first and second monomeric subunits include about 77.5 percent by weight of the copolymer. In some embodiments, the first and second monomeric subunits include about 85 percent by weight of the copolymer.

In the present copolymers, the total quantity of the one or more of the third and fourth monomeric subunits will make up a minority of the polymer, as measured by weight.

In some embodiments, the copolymers provided herein may include about 5 to about 30 percent by weight of the third monomeric subunit based on the total weight of the copolymer. In some embodiments, the third monomeric subunit may include about 5-10 percent, about 5-15 percent, about 5-20 percent, or about 5-25 percent by weight of the copolymer. In some embodiments, third monomeric subunit may include about 5 percent, about 6 percent, about 7 percent, about 8 percent, about 9 percent, about 10 percent, about 11 percent, about 12 percent, about 13 percent, about 14 percent, about 15 percent, about 16 percent, about 17 percent, about 18 percent, about 19 percent, about 20 percent, about 21 percent, about 22 percent, about 23 percent, about 24 percent, about 25 percent, about 26 percent, about 27 percent, about 28 percent, about 29 percent, or about 30 percent by weight of the copolymer. In some embodiments, the third monomeric subunit includes about 10 percent by weight of the copolymer. In some embodiments, the third monomeric subunit includes about 15 percent by weight of the copolymer.

In some embodiments, the copolymers provided herein may include about 0 to 15 percent by weight of the fourth monomeric subunit based on the total weight of the copolymer. In some embodiments, the fourth monomeric subunit may include about 5 to 10 percent or about 7 to 10 percent by weight of the copolymer. In some embodiments, the fourth monomeric subunit may include about 5 percent, about 6 percent, about 7 percent, about 8 percent, about 9 percent, about 10 percent, about 11 percent, about 12 percent, about 13 percent, about 14 percent, or about 15 percent by weight of the copolymer. In some embodiments, the fourth monomeric subunit may include about 7.5 percent by weight of the copolymer.

In some embodiments, the copolymers provided herein may include about 0% by weight of the fourth monomeric subunit based on the total weight of the copolymer.

In some embodiments, the fourth monomeric subunit has a higher molecular weight and therefore can provide reduction of glistening by use of a smaller number of molecules while also not substantially increasing the $T_g$ of the final polymeric material.

In some embodiments, the fourth monomeric subunit includes 200 PEG MW.

In some embodiments, the total quantity of the combined amounts of the third and fourth monomeric subunits may be about 10 percent to about 45 percent by weight of the total weight of the polymer. In some embodiments, the third and fourth monomeric subunits may include about 10-15 percent, about 10-20 percent, about 10-25 percent, about 10-30 percent, about 10-35 percent, or about 10-40 percent by weight of the copolymer. In some embodiments, the third and fourth monomeric subunits include about 10-20 percent, about 20-30 percent, about 30-40 percent, or about 30-45 percent by weight of the copolymer. In some embodiments, the third and fourth monomeric subunits include about 10 percent, about 11 percent, about 12 percent, about 13 percent, about 14 percent, about 15 percent, about 16 percent, about 17 percent, about 18 percent, about 19 percent, about 20 percent, about 21 percent, about 22 percent, about 23 percent, about 24 percent, about 25 percent, about 26 percent, about 27 percent, about 28 percent, about 29 percent, about 30 percent, about 31 percent, about 32 percent, about 33 percent, about 34 percent, about 35 percent, about 36 percent, about 37 percent, about 38 percent, about 39 percent, or about 40 percent, about 41 percent, about 42 percent, about 43 percent, about 44 percent, or about 45 percent by weight of the copolymer.

In some embodiments, the copolymers provided herein may include about 0-25 percent by weight of the fifth monomeric subunit based on the total weight of the copolymer. In some embodiments, the fifth monomeric subunit may include about 0-10 percent, about 0-15 percent, or about 0-20 percent by weight of the copolymer. In some embodiments, the fifth monomeric subunit may include about 0 percent, about 1 percent, about 2 percent, about 3 percent, about 4 percent, about 5 percent, about 6 percent, about 7 percent, about 8 percent, about 9 percent, about 10 percent, about 11 percent, about 12 percent, about 13 percent, about 14 percent, about 15 percent, about 16 percent, about 17 percent, about 18 percent, about 19 percent, about 20 percent, about 21 percent, about 22 percent, about 23 percent, about 24 percent, or about 25 percent by weight of the copolymer. In some embodiments, the fifth monomeric subunit may include about 20 percent by weight of the copolymer.

In some embodiments, the fifth monomeric subunit includes EOEMA.

In the present copolymers, the total quantity of the one or more of the crosslinking monomeric subunit will make up a minority of the copolymer. For example, in some embodiments, the total quantity of the combined amounts of incorporated crosslinking monomeric subunit ranges from about 0.5 percent to 3.0 percent by weight based on the total weight of the copolymer. In some embodiments, the crosslinking monomeric subunit may include about 0.5-1.0 percent, about 0.5-1.5 percent, about 0.5-2.0 percent, or about 0.5-2.5 percent by weight of the copolymer. In some embodiments, the crosslinking monomeric subunit may include about 0.5 percent, about 0.6 percent, about 0.7 percent, about 0.8 percent, about 0.9 percent, about 1.0 percent, about 1.1 percent, about 1.2 percent, about 1.3 percent, about 1.4 percent, about 1.5 percent, about 1.6 percent, about 1.7 percent, about 1.8 percent, about 1.9 percent, about 2.0 percent, about 2.1 percent, about 2.2 percent, about 2.3 percent, about 2.4 percent, about 2.5 percent, about 2.6 percent, about 2.7 percent, about 2.8 percent, about 2.9 percent, or about 3.0 percent by weight of the copolymer. In some embodiments, the crosslinking monomeric subunit may include about 2.74 percent by weight of the copolymer.

In some embodiments, the crosslinking monomeric subunit includes TMPTMA.

When a polymer or copolymer is said to include or contain a monomeric subunit such as ethoxyethyl methacrylate, it will be understood that this means that the ethoxyethyl methacrylate monomeric subunit has been reacted and incorporated into the polymer. A monomeric subunit of the claimed compounds may also be in the form of an oligomer that can be polymerized into the embodied copolymeric compounds.

In some embodiments, the copolymers may include about 50% to about 60% of the first monomer, about 20% to about 30% of the second monomer, about 10% or less of the third monomer, about 5% to 10% of the fourth monomer, and about 0% to about 5% of the crosslinker. In some embodiments, the copolymers may include about 50% to about 60% of EOEOEMA, about 20% to about 30% of BrHPPMA, about 10% of HPPMA, about 5% to 10% of 200 PEG MW, and about 0% to about 5% of TMPTMA. In some embodiments, the copolymers may include about 57.5% of the first monomer, about 25% of the second monomer, about 10% of the third monomer, about 7.5% of the fourth monomer, and about 2.74% of the crosslinker. In some embodiments, the copolymers may include about 57.5% of EOEOEMA, about 25% of BrHPPMA, about 10% of HPPMA, about 7.5% of 200 PEG MW, and about 2.74% of TMPTMA.

In another embodiment, the compositions of the preceding paragraph comprise polymerized alkoxyalkoxyalkyl methacrylamide and/or polymerized alkoxyalkoxyalkyl acrylamide as a first monomeric subunit in place of the polymerized alkoxyalkoxyalkyl methacrylate and/or polymerized alkoxyalkoxyalkyl acrylate.

In some embodiments, the copolymer compositions of the present embodiments consist of or consist essentially of a copolymer formed from an alkoxyalkoxyalkyl (meth)acrylate, a hydroxyl and halogen-substituted aryloxyalkyl (meth)acrylate, a hydroxy-substituted aryloxyalkyl (meth)acrylate, a polyalkylene glycol alkylether methacrylate and one or more crosslinking agent.

In some embodiments, the copolymer is formed from monomeric subunits consisting of 2-ethoxyethoxyethyl methacrylate, bromo-2-hydroxy-3-phenoxypropyl methacrylate, 2-hydroxy-3-phenoxypropyl methacrylate, polyethylene glycol monomethyl ether methacrylate, and TMPTMA.

In some embodiments, a copolymer comprises, consists essentially of, or consists of:

(a) an incorporated alkoxyalkoxyalkyl (meth)acrylate such as 2-ethoxyethoxyethyl methacrylate in an amount of from about 40 to 65 percent;

(b) an incorporated hydroxy and halogen-substituted aryloxyalkyl (meth)acrylate such as bromo-2-hydroxy-3-phenoxypropyl methacrylate in an amount of from about 15 to 30 percent;

(c) an incorporated hydroxy-substituted aryloxyalkyl (meth)acrylate such as 2-hydroxy-3-phenoxypropyl methacrylate in an amount of from about 5 to 30 percent;

(d) an incorporated polyethylene glycol monomethyl ether methacrylate such as PEG200M or PEG400M in an amount of from 5 to 15 percent;

(e) optionally, one or more optional other ingredients such as water, one or more UV absorbing compound or monomer, a colorant, and an antioxidant.

In some embodiments, the first, second, and third monomeric subunits together comprise about 70, 75, 80, 85, and/or 90 percent or more of the monomeric subunits composition by weight.

Weight Ratios

In some embodiments, the compositions of the disclosure may conform with one or more of the following three ratios of components:

First Ratio: short-chain aliphatic monomers to aromatic monomers;
Second Ratio: First Monomer to Fifth Monomer (e.g., the short-chain aliphatic monomers);
Third Ratio: Second Monomer to Third Monomer (e.g., the aromatic monomers).

Without being bound by theory, the adjustment of the First Ratio is believed to allow the user to tune mechanical properties by having a relatively high aliphatic content. The second Ratio allows the user to adjust Tg while maintaining the beneficial mechanical properties. The Third Ratio allows the user to maintain a high refractive index while maintaining the beneficial mechanical properties and/or desired Tg.

In some embodiments, the Second ratio is adjusted so that the Tg is changed while while mechanical properties and/or Abbe value and/or refractive index are substantially the same. In some embodiments, the Third Ratio is adjusted so that the refractive index is increased while mechanical properties and/or Abbe value and/or Tg are substantially the same.

In some embodiments, the First Ratio is greater than 1:1. In some embodiments, the copolymers provided herein may include a combination of short chain aliphatic monomers and aromatic monomers such that the co-polymers have low glass transition temperatures but high refractive indices. In some embodiments, the copolymers may include from about 30% to about 65% of short chain aliphatic monomers; about 15% to about 65% of aromatic monomers; and about 5% to about 15% of other monomers. In some embodiments, the copolymers may include about 35% to about 65%, about 40% to about 65%, about 45% to about 65%, about 50% to about 65%, about 55% to about 65%, or about 60% to about 65% of short chain aliphatic monomers. In some embodiments, the copolymers may include about 15% to about 60%, about 15% to about 55%, about 15% to about 50%, about 15% to about 45%, about 15% to about 40%, about 15% to about 35%, about 15% to about 30%, about 15% to about 25%, about 15% to about 20% of aromatic monomers. In some embodiments, the glass transition temperature of the copolymer can be lowered by increasing the amount of short chain aliphatic monomers. In some embodiments, the refractive index of the co-polymer can be increased by increasing the amount of aromatic monomers. In some embodiments, the respective amounts of the short chain aliphatic monomers and the aromatic monomers can be altered to achieve a copolymer with a desired low glass transition temperature and a desired high refractive index. In some embodiments, the copolymers may include a combination of short chain aliphatic monomers and aromatic monomers such that the copolymers have a glass transition temperature of less than 15° C., 14° C., 13° C., 12° C., 11° C., 10° C., 9° C., 8° C., 7° C., 6° C., 5° C., 4° C., 3° C., 2° C., 1° C., 0° C., −1° C., −2° C., −3° C., −4° C., or −5° C. In some embodiments, the copolymers may include a combination of short chain aliphatic monomers and aromatic monomers such that the copolymers have a refractive index value of 1.48, 1.49, 1.50, 1.51, 1.52, or 1.53. In some embodiments, the copolymers may include not less than 30% of short chain aliphatic monomers and not more than 30% of aromatic monomers such that the copolymers have a glass transition temperature of less than 10° C. and a refractive index of at least 1.50.

In some embodiments, the ratio of the first monomeric subunit to the second and third monomeric subunits provides for high refractive index and low glass transition temperature of the copolymers provided herein. In some embodiments, the ratio of the first monomeric subunit to the second and third monomeric subunits is equal to or greater than one. In other words, in some embodiments, the copolymers provided herein may include an equivalent or higher amount of the first monomeric subunit than the second and third monomeric subunits. In some embodiments, the ratio of the first monomeric subunit to the second and third monomeric subunits is 1.0, 1.1, 1.2, 1.3, 1.4, 1.5, 1.6, 1.7, 1.8, 1.9, 2.0, 2.1, 2.2., 2.3, 2.4, 2.5, 2.6, 2.7, 2.8, 2.9, 3.0, 3.1, 3.2, 3.3, 3.4, or 3.5:1.

In some embodiments, the Second Ratio is 1:1 to 1:0. That is, the First monomer is a majority of the total of the First and Fifth monomers. In some embodiments, the Fifth monomer is not present.

In some embodiments, the Third Ratio (i.e., the ratio of the second monomeric subunit to the third monomeric subunit) provides for the ability to vary RI while keeping mechanical properties, such as Tg and Abbe number, constant low glass transition temperature of the copolymers provided herein. In some embodiments, the ratio of the second monomeric subunit to the third monomeric subunit is greater than one. In other words, in some embodiments, the copolymers provided herein may include a higher amount of the second monomeric subunit than the third monomeric subunit. In some embodiments, the ratio of the second monomeric subunit to the third monomeric subunit is 1.5, 1.6, 1.7, 1.8, 1.9, 2.0, 2.1, 2.2, 2.3, 2.4, or 2.5:1.

The short chain aliphatic monomers may include, e.g., the First and Fifth monomers disclosed above, for example, EOEOEMA and EOEMA may comprise or consist of the short chain aliphatic monomers. The aromatic monomers may include, e.g., the Second and Third monomers disclosed above, for example, Br-HPPMA and HPPMA.

Properties of Composition

The copolymers can have a water content of less than or about 5 percent, or less than about 3 percent, based on the weight of the copolymer after it is fully equilibrated in water. In some embodiments, the copolymers have a water content at equilibrium that ranges from at or about 1 percent to at or about 5 percent based on the weight of the copolymer after it is fully equilibrated in water. In other embodiments, the water content ranges from about 2 percent to about 4 percent by weight of the copolymer after it is fully equilibrated with water.

The copolymers can possess superior mechanical and optical properties over other materials used to make IOLs, for example an increased refractive index over the prior art, which also remain foldable, low in glistenings and high in Abbe value. The components of present embodiments can provide for a hydrophobic lens with low $T_g$, reduced glistenings and reduced stickiness providing for an IOL with desirable and reliable unfolding times, while maintaining a high refractive index.

The copolymers can be designed to have a wide range of physical characteristics. In some instances, the present copolymers can be designed to have glass transition temperatures below at or about 35° C., below at or about 30° C., below at or about 25° C., such as from at or about −25° C. to at or about 35° C., 30° C., or 25° C., from about −5° C. to about 5° C., 10° C., 15° C., 20° C., or about 25° C., or from at or about 0° C. to at or about 15° C. In some embodiments, the glass transition temperature will be from about 0° C. to about 10° C., from about 0° C. to about 8° C., from about 0° C. to about 5° C., or from about 0° C. to about 3° C. In preferred embodiments, the glass transition temperature will be from about −5° C. to about 5° C. In preferred embodiments, the glass transition temperature will be less than about 10° C., 9° C., 8° C., 7° C., 6° C., 5° C., 4° C., 3° C., 2° C., 1° C., 0° C., −1° C., −2° C., −3° C., −4° C., or about −5° C. Glass transition temperatures referred to herein may be measured at half width at a temperature change rate of 10° C./minute, or other methods known in the art.

As the present copolymers have been designed to be used as intraocular lenses, they also typically have a high refractive index, which is generally above about 1.46 or above 1.50. Some of the present copolymers can have a refractive index of 1.48 or higher. Some of the present copolymers can have a refractive index of 1.50 or higher. In some embodiments, the copolymers provided herein have a refractive index of 1.50, 1.51, 1.52, or 1.53.

Because the present copolymers are hydrophobic, they can also have equilibrium water contents that are about 5 percent or less, for example 4 percent, 3 percent, 2 percent, 1 percent or less. Due to their low water contents, the present copolymers are generally not considered hydrogels and may be considered as hydrophobic. Generally, the present lenses also have advantageous properties compared to prior lenses because they have a comparable or higher refractive index than lenses containing silicone or p-hydroxyethyl methacrylate and are more flexible, e.g., foldable, than hydrophobic lenses that include aromatic monomeric subunits to increase the refractive index of the resulting polymer.

In some embodiments, the present copolymers can have an Abbe value of greater 45, or 46. In some embodiments, the present copolymers can have an Abbe value of 45, 46, 47, 48, or 49. In some embodiments, the present copolymers can have an Abbe value of 47. The human lens has an Abbe value of about 47. A high Abbe value indicates low chromatic aberration, which is a desirable quality for IOLs. Accordingly, in certain embodiments, the IOLs of the present disclosure have an Abbe value of 45, 46, 47, 48, or 49.

In some embodiments, the Abbe value can be measured by the following formula:

$$\text{Abbe Value} = (\text{Refractive Index at 589 nm} - 1) / (\text{Refractive Index at 486 nm} - \text{Refractive Index at 656 nm})$$

In some embodiments, the copolymers provided herein have a SI value of less than 850. In some embodiments, the copolymers provided herein have a SI value of from about 600 to about 850. In some embodiments, the copolymers provided herein have a SI value of less than 825, 800, 775, 750, 725, 700, 675, 650, or 625 as measured on the Trattler severity index.

Lens

A present embodiment also provides intraocular lenses made at least partially from the present copolymers. Such intraocular lenses include an optic portion and one or more haptic portions. Typically, the copolymers of the embodiments will make up part or the entire optic portion of the intraocular lens. In some embodiments, the optic portion of the lens will have a core made from one of the present copolymer surrounded by different polymer or material. Lenses in which the optic portion is made up of at least partially of one of the present copolymers will usually also have a haptic portion. The haptic portion can also be made of copolymer of the embodiments or can be made of a different material, for example another polymer.

In some embodiments, the present intraocular lens is a one-piece lens having a soft, foldable central optic region and an outer peripheral region (haptic-region) in which both regions are made of the same polymer. In other embodiments, the optic and haptic regions can be formed from different types of polymers or materials, if desired. Some lenses can also have haptic portions that are made up of different materials, for example where one or more haptic portions is made from the same material as the optic portion and other haptic portions are made of materials other than a polymer of the embodiments. Multicomponent lenses can be made by embedding one material in the other, concurrent extrusion processes, solidifying the hard material about the soft material, or forming an interpenetrating network of the rigid component into a preformed hydrophobic core. In instances where one or more haptic portions are made from a different material than the optic portion of the lens, the haptic portion can be attached to the optic portion in any manner known in the art, such as by drilling a hole or holes in the optic portion and inserting the haptic portion.

The copolymers of the present embodiments can be designed so that they are capable of being folded so that the intraocular lens can be inserted into the eye of an individual through a small incision. The haptic portion of the lens provides the required support for the lens in the eye after insertion and unfolding of the lens and tends to help stabilize the position of the lens after insertion and the closure of the incision. The shape of the haptic portion design is not particularly limited and can be any desired configuration, for example, either a plate type or graduated thickness spiral filaments, also known as a C-loop design.

The optic portion of an IOL can be approximately 6 mm in diameter prior to hydration. The 6 mm diameter is fairly standard in the art, and is generally chosen to cover the pupil in its fully dilated state under naturally occurring conditions. However, other sizes are possible and the present embodiments are not limited to any particular diameter or size of intraocular lens. Furthermore, it is not necessary that the lens optic portion be circular; it could also be oval, square, or any other shape as desired.

The intraocular lens can further include one or more non-optical haptic components of an IOL extending away from the outermost peripheral surface of the optic portion. The haptic components can be of any desired shape, for example, graduated spiral filaments or flat plate sections and are used to support the lens within the posterior chamber of the eye. Lenses having any desired design configuration can be fabricated. Further, the haptics can have configurations other than those illustrated. Should the intraocular lens include other components besides the optical and haptic portions, such other portions can be made of a polymer as are the haptic and optic portions, or if desired, another material.

The intraocular lenses of the embodiments may be inserted into the eye in known manners. For example, the intraocular lens may be folded prior to insertion into the eye by small, thin forceps of the type typically used by ophthalmic surgeons. After the lens is in the targeted location, it is released to unfold. As is well known in the art, typically the lens that is to be replaced is removed prior to insertion of the intraocular lens. The intraocular lens of the present embodiments can be made of a generally physiologically inert soft polymeric material that is capable of providing a clear, transparent, refractive lens body even after folding and unfolding. In some embodiments, the foldable intraocular lens of the present embodiments can be inserted into any eye by injection whereby the mechanically compliant material is folded and forced through a small tube such as a 1 mm to 3 mm inner diameter tube. In one embodiment the small tube has an inner diameter of approximately 2.0 or 1.9 or 1.8 or 1.7 or 1.6 or 1.5 mm or less. In one embodiment the inner diameter is approximately 1.4 to 2.0 mm. In one embodiment, the inner diameter is approximately 1.8 mm, in another it is 1.6 mm. In one embodiment, the finished IOL lens is microinjectable (e.g. able to be injected through a small tube that has an inner diameter of approximately 1.8 mm or 1.6 mm).

Methods of Making Composition

The copolymers of the embodiments herein can be prepared using conventional polymerization techniques known to those in the field of polymer chemistry. Crosslinkers, also referred to as crosslinking agents, may be employed in the polymerization reaction. For example, any suitable crosslinking di-functional, multi-functional monomer, or combination of these can be used in effective amounts to give the desired crosslinking density. For example, in a concentration range of 0.5 to about 5 (e.g., about 2 to about 3 or about 2.5 to about 3) percent by weight based on the weight of the dry copolymer. Examples of suitable crosslinking agents include di-olefinic compounds such as ethylene glycol dimethacrylate (EGDMA) and tetraethylene glycol dimethacrylate (TEGDMA) and other cross-linking agents such as trimethylol propane trimethacrylate (TMPTMA) which include three or more olefinic polymerizable functionalities. Generally, crosslinkers help to enhance the resulting polymer's dimensional stability.

Also, if desired an initiator can be used in the polymerization. Any initiator commonly used in the art, such as azo derivatives, like 2,2-azobis (2,4-dimethylvaleronitrile) and propanenitrile, 2-methyl,2,2'-azobis, can be used. The initiator may also be a photo initiator, a thermal initiator, or other type of initiator as recognized by one skilled in the art. In some embodiments, the photo initiator is CGI 819. The initiator is used in an amount effective for initiation purposes, and is generally present from about 0.01 to 1.0 percent by weight, based on the weight of the polymer.

The copolymers of the present embodiments can also include additional monomers, such as, but not limited to, monomers that impart ultraviolet (UV) absorption to the polymer and/or monomers that impart absorption to the lens, such as blue light-blocking. UV absorbing monomers are typically aromatic compounds with olefinic functionality. The advantageous UV absorbing compounds can be added prior to polymerization for incorporation into the resultant polymer, as is well known in the art. The UV absorber should preferably be capable of polymerization into the lens matrix so as to be stable under physiological conditions. Any monomer copolymerizable with the described monomeric subunits can optionally be used, so long as such monomer does not materially or adversely affect the basic characteristics of the intraocular lens. Examples of useful additional monomers that can be used are described in U.S. Pat. No. 5,326,506, hereby incorporated by reference, directed to a composite intraocular lens. Additionally, aryl-substituted triazole compounds, such as for example, tris-aryl triazole compounds described in U.S. Pat. No. 6,365,652, may be used in at low concentrations to achieve desired UV absorbing properties. Such optional additional monomers, preferably are present in a total amount of not more than 10 weight percent, generally less than 5 weight percent, based on the total weight of the polymer.

In some embodiments, the polymerization reaction is conducted without any solvent.

As described above, it may be useful to add crosslinking agents such as EGDMA, TEGDMA, or TMPTMA, for example, to enhance the resulting polymer's dimensional stability. It may also be advantageous to add UV absorbing compounds with the lens monomeric subunits prior to polymerization for incorporation into the resultant polymer. The UV absorber should preferably be capable of polymerization into the lens matrix so as to resist extraction under physiologic conditions. The UV-absorbing monomer can be present in an amount effective to give the desired UV-absorbing properties, generally less than 4 percent by weight of the polymer, such as from 0.01 to about 1 percent by weight of the polymer. UV absorbers include those known in the art, such as, Natural Yellow, benzotriazoles, those in U.S. Ser. No. 13/619,043, and the like.

Examples of specific copolymers useful in the present embodiments are included in Table 1 which are also discussed in the examples where all weights used in the polymerization are shown in grams with the percentage of the monomeric subunits in the polymer shown in parenthesis based on the total of all monomeric subunits and crosslinking agents and assuming incorporation of all monomeric subunits and crosslinkers in the copolymers.

Formation of Intraocular Lens

The intraocular lenses of the present embodiments may be formed by methods known in the art. For example, in an exemplary process, the monomeric subunits that form the copolymer are polymerized into a polymer rod, polymer blanks or discs are formed from the rod, and then the blanks are cut, for example, by a lathe into the intraocular lens. The rods can be made by a procedure which begins with polymerizing, in a mold, such as in a tubular or cylindrical mold, a mixture of initiator and monomeric subunits, to form an optically clear soft lens body. As discussed above, it may be desirable to incorporate cross-linking materials and ultraviolet-absorbing compounds during polymerization or into the resultant polymer matrix. In some embodiments, the polymer rods are then cut and ground or otherwise machined, into blanks of the desired diameter and thickness by lathe cutting and machine milled at temperatures below the $T_g$ into an intraocular lens.

Generally, the composite material rod is lathe cut or ground to a diameter 0.5 to 2.0 mm thicker than the required distance from the center of the lens body to the furthest edge of the legs or haptics. This rod is then cut into blanks of uniform thickness. The blanks are ground and lapped to a diameter and thickness suitable for lathe cutting and machine milling in the conventional manner into the intraocular lens of the present embodiments. Because the present copolymers may have low glass transition temperatures, the rod or blanks may require cooling below $T_g$ prior to and/or during cutting, lathing and/or milling.

A general description of a stepwise process for forming the blanks into intraocular lenses is set forth in the flow chart below. One having ordinary skill in the field of intraocular lens manufacturing, from a review of the present specification, can make intraocular lenses using the general knowledge in the art on intraocular lens manufacture and the process of cryogenic machining.

Intraocular lenses can also be made by molding the present copolymer to form all or part of the optic portion of the lens. For example, the present copolymer can be polymerized in a mold by a liquid mixture of monomeric subunits and additional components, to form an optically clear soft lens body. These molding methods can involve molding the optics on one half of the lens, such as the anterior or posterior portion, or fully molding the lens. When only half of the optic portion of the lens is formed in the mold then the second side optics can be machined, for example as discussed above. In either of these embodiments, additional material can be molded to allow machining of various haptic designs. The copolymer may be optionally molded in the form of a preformed lens as known in the art as a universal blank.

Polymer Does Not Comprise Components

In one embodiment, the copolymer composition does not comprise a fourth monomeric subunit which is a hydrophilic, low molecular weight monomer having a molecular weight of less than about 150 g/mol, or less than about 100 g/mol.

For example, in one embodiment, the copolymer composition does not comprise polymerized hydroxyethylacrylate (HEA). In one embodiment, the copolymer composition does not comprise polymerized glycidyl methacrylate (GMA). In one embodiment, the copolymer composition does not comprise the combination of HEA and GMA.

In one embodiment, the copolymer composition does not comprise a fifth monomeric subunit which is an alkoxyalkyl (meth)acrylate.

Applications

One application is lens, including lens adapted for the human eye, including IOLs.

Additional embodiments are provided in the following non-limiting working examples and contrasted with comparative examples.

WORKING EXAMPLES

HPPMA refers to 2-hydroxy-3-phenoxypropyl methacrylate

Br-HPPMA refers to 4-bromo-2-hydroxy-3-phenoxypropyl methacrylate

EOEOEA refers to ethoxyethoxyethyl acrylate

EOEOEMA refers to ethoxyethoxyethyl methacrylate

EOEMA refers to 2-ethoxyethyl methacrylate PEG200M refers to polyethylene glycol monomethyl ether methacrylate (200 PEG MW)

PEG400M refers to polyethylene glycol monomethyl ether methacrylate (400 PEG MW)

TMPTMA refers to trimethylol propane trimethacrylate

Example 1

Preparation of 4-bromo-2-hydroxy-3-phenoxypropyl methacrylate

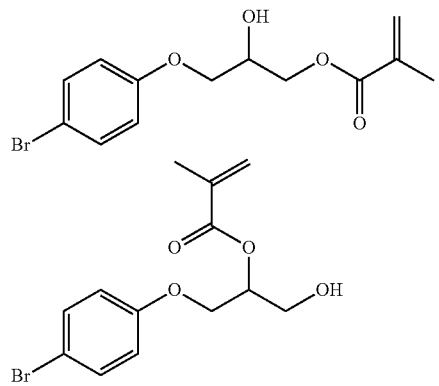

Scheme 1.

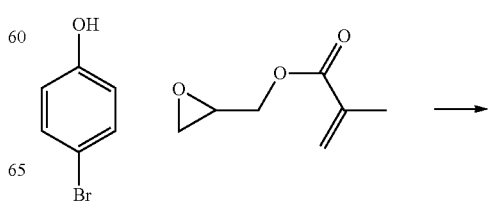

-continued

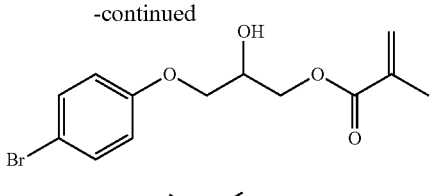

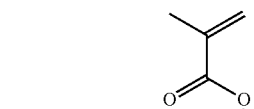

| Reactant/Solvent | Mol Wt. | Mass (g) | Vol (L) | Mol | eq. |
|---|---|---|---|---|---|
| 4-bromoPhenol | 173.01 | 100 | | 0.58 | |
| Glycidyl methacrylate (GMA) | 142.15 | 107 | | 0.75 | 1.3 |
| Tetraethylammonium bromide (TEAB) | 210.36 | 24 | | 0.12 | 0.2 |
| DMF, anhydrous | | | 1 | | |

Under N$_2$, 4-bromophenol, anhydrous DMF was added into flask at room temp. TEAB, and GMA with anhydrous DMF (Total 1 L) was added. The mixture was slowly heated to 70° C. and kept at 70 ° C. for 2 days. Thin layer chromatography (TLC) showed no more staring material and only product. The reaction mixture was cooled to room temp. Water (2 L) was added. The extraction was carried out by using ethyl acetate (EtOAc) (2×1L). The EtOAc layers were washed with 10% KOH aqueous and then water and then dried over anhydrous Na$_2$SO$_4$. The organic layers were filtered. The solvent was removed. The residue was purified by column chromatography on silica gel, eluting with hexanes (hex), and then 5% EtOAc/hex. 87 g of white solid was collected. The white solid was dissolved in CH$_2$Cl$_2$ (200 mL). The CH$_2$Cl$_2$ solution was washed with 10% KOH aqueous, and then water. Solvent was removed. The solid was dissolved in acetone (20 mL). Hexane (100 mL) was added until the solution turning cloudy (1 drop of acetone turned it to be clear). This solution was kept at room temp for overnight, and the white solid was precipitated. The solution was filtered and dried. The white solid was collected (45 g): mp: 68-69 ° C.; HPLC: 99.7%; GC: 100%.

Acid content test: Methanol/water (2:1, 200 mL) was neutralized with 0.02 N NaOH aqueous with phenolphthalein. 2 g of the product was added to be dissolved. The NaOH aqueous (0.02 N) was added and the red color was not disappeared within 1 minute.

Example 2

Preparation of 2-hydroxy-3-phenoxypropyl methacrylate

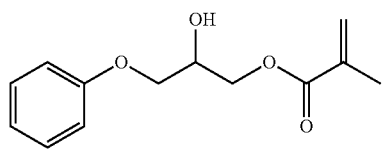

-continued

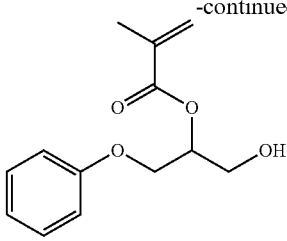

Scheme 2.

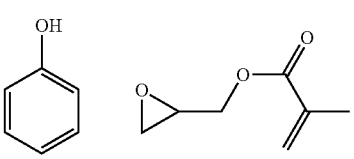

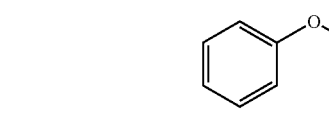

| Reactant/Solvent | Mol Wt. | Mass (g) | Vol (L) | Mol | eq. |
|---|---|---|---|---|---|
| Phenol | 94.11 | 188 | | 2.0 | |
| GMA | 142.15 | 370 | | 2.6 | 1.3 |
| Tetraethylammonium bromide (TEAB) | 210.36 | 84 | | 1.4 | 0.2 |
| DMF, anhydrous | | | 1.5 | | |

Under N$_2$, phenol, anhydrous DMF was added into flask at room temp. TEAB, and GMA with anhydrous DMF (Total 1.5 L) was added. The mixture was slowly heated to 70° C. and kept at 70° C. for 2 days. TLC showed no more staring material and only product. The reaction mixture was cooled to room temp. Water (2 L) was added. The extraction was carried out by using EtOAc (3×1 L). The EtOAc layers were washed with 10% KOH aqueous and then water and dried over anhydrous Na$_2$SO$_4$. The organic layers were filtered. The solvent was removed. The residue was purified by column chromatography on silica gel, eluting with hex, and then 5% EtOAc/hex. 210 g of colorless oil was collected. The crude oil was dissolved in CH$_2$Cl$_2$ (300 mL). The CH$_2$Cl$_2$ solution was washed with 10% KOH aqueous, and then water. Solvent was removed. The oil was dissolved in acetone (50 mL). Hexane (300 mL) was added until the solution turning cloudy (1 drop of acetone turned it to be clear). This solution was kept in refrigerator for 2 days, and was shaken very often until the white solid was precipitated. The solution was filtered, dried. The white solid was collected (135 g): mp: 28-29° C.; HPLC: 99.6%; GC: 99.1%.

Acid content test: Methanol/water (2:1, 200 mL) was neutralized with 0.02 N NaOH aqueous with phenolphthalein. 2 g of the product was added to be dissolved. The NaOH aqueous (0.02 N) was added and the red color was not disappeared within 1 minute.

Polymer Examples

Unless otherwise noted, the following polymerizations were conducted on a 4-5 g scale.

Example 3

25 wt. % of Br-HPPMA was mixed with 10 wt. % of HPPMA, 57.5 wt. % of EOEOEMA, 7.5 wt. % of PEG200M, and 2.7 wt. % of TMPTMA. The homogenous mixture was degassed. The mixture was dispensed into molds and photo-cured at 2.5 mW/cm$^2$ for 60 min at 30° C. (pulsed in 10 min intervals) followed by 3.0 mW/cm$^2$ for 10 min at 75° C. The molds were allowed to cool to room temperature. The molds were opened and the polymer disc was removed and inspected. The polymer displayed properties summarized in Table 1.

Example 4

25.0 wt. % of Br-HPPMA was mixed with 10.0 wt. % of HPPMA, 57.5 wt. % of EOEOEMA, 7.5 wt. % of PEG200M, and 2.7 wt. % of TMPTMA. The homogenous mixture was degassed. The mixture was dispensed into molds and photo-cured at 0.25 mW/cm$^2$ for 60 min at 25-40° C. and then 3.0 mW/cm$^2$ for 10 min at 75° C. The molds were allowed to cool to room temperature. The molds were opened and the polymer disc was removed and inspected. The polymer displayed properties summarized in Table 1.

Example 5

25.0 wt. % of Br-HPPMA was mixed with 10.0 wt. % of HPPMA, 57.5 wt. % of EOEOEMA, 7.4 wt. % of PEG200M, 2.7 wt. % of TMPTMA. The mixture was filtered through a 0.1 μm filter and degassed. The mixture was dispensed into molds and photo-cured at 0.25 mW/cm$^2$ for 60 min at 40° C. and then 3.0 mW/cm$^2$ for 10 min at 75° C. The molds were allowed to cool to room temperature. The molds were opened and the polymer disc was removed and inspected. The polymer displayed properties summarized in Table 1.

Example 6

On a 20 gram scale, 25.0 wt. % of Br-HPPMA was mixed with 10.0 wt. % of HPPMA, 57.5 wt. % of EOEOEMA, 7.4 wt. % of PEG200M, 2.7 wt. % of TMPTMA. The mixture was filtered through a 0.1 μm filter and degassed. The mixture was dispensed into molds and photo-cured at 0.25 mW/cm$^2$ for 60 min at 40° C. and then 3.0 mW/cm$^2$ for 10 min at 75° C. The molds were allowed to cool to room temperature. The molds were opened and the polymer disc was removed and inspected. The polymer displayed properties summarized in Table 1.

Example 7

25.0 wt. % of Br-HPPMA was mixed with 10.0 wt. % of HPPMA, 15 wt. % EOEMA, 42.5 wt. % of EOEOEMA, 7.4 wt. % of PEG200M, 2.7 wt. % of TMPTMA. The mixture was filtered through a 0.1 μm filter and degassed. The mixture was dispensed into molds and photo-cured at 0.25 mW/cm$^2$ for 60 min at 40° C. and then 3.0 mW/cm$^2$ for 10 min at 75° C. The molds were allowed to cool to room temperature. The molds were opened and the polymer disc was removed and inspected. The polymer displayed properties summarized in Table 1.

Example 8

25.0 wt. % of Br-HPPMA was mixed with 10.0 wt. % of HPPMA, 12 wt. % EOEMA, 45.5 wt. % of EOEOEMA, 7.4 wt. % of PEG200M, 2.7 wt. % of TMPTMA. The mixture was filtered through a 0.1 μm filter and degassed. The mixture was dispensed into molds and photo-cured at 0.25 mW/cm$^2$ for 60 min at 40° C. and then 3.0 mW/cm$^2$ for 10 min at 75° C. The molds were allowed to cool to room temperature. The molds were opened and the polymer disc was removed and inspected. The polymer displayed properties summarized in Table 1.

TABLE 1

| Example # | Refractive Index (35° C.) | Tg (° C.) | Abbe Value | SI |
|---|---|---|---|---|
| 3 | 1.5114 | 1 | 48.5 | 700 |
| 4 | 1.5112 | 2 | 48.0 | 640 |
| 5 | 1.5118 | 1 | 48.0 | 720 |
| 6 | 1.5113 | 1 | 47.6 | 725 |
| 7 | 1.5117 | 8 | 47.9 | 690 |
| 8 | 1.5116 | 6 | 48.1 | 708 |

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all sub ratios falling within the broader ratio.

One skilled in the art will also readily recognize that where members are grouped together in a common manner, such as in a Markush group, the present embodiments encompasses not only the entire group listed as a whole, but each member of the group individually and all possible subgroups of the main group. Accordingly, for all purposes, the present embodiments encompass not only the main group, but also the main group absent one or more of the group members. The present embodiments also envisage the explicit exclusion of one or more of any of the group members in the claimed embodiments.

All references, patents and publications disclosed herein are specifically incorporated by reference in their entireties and for all purposes as if fully set forth in their entireties. Unless otherwise specified, "a" or "an" means "one or more".

While preferred embodiments have been illustrated and described, it should be understood that changes and modifications can be made therein in accordance with ordinary skill in the art without departing from the embodiments in its broader aspects as defined in the following claims.

What is claimed is:

1. A composition comprising at least one co-monomer mixture comprising:
   (a) a first monomeric subunit comprising a polymerized (meth)acrylate group and at least one alkoxyalkoxyalkyl side group,
   (b) a second monomeric subunit different from the first monomeric subunit comprising a polymerized (meth)acrylate group, at least one side group comprising (i) an aryloxy moiety comprising at least one halogen, and (ii) an aliphatic carbon moiety linking the aryloxy moiety with the polymerized (meth)acrylate group, wherein the aliphatic carbon moiety comprises at least one hydroxyl substituent,
   (c) a third monomeric subunit different from the first and second monomeric subunits comprising a polymerized (meth)acrylate group, at least one side group comprising (i) an aryloxy moiety, and (ii) an aliphatic carbon moiety linking the aryloxy moiety with the polymerized (meth)acrylate group, wherein the aliphatic carbon moiety comprises at least one hydroxyl substituent,
   (d) optionally a fourth monomeric subunit different from the first, second, and third monomeric subunits comprising a polymerized acrylate or (meth)acrylate group, and at least one alkylene oxide side group, and
   (e) optionally a fifth monomeric subunit different from the first, second, third, and fourth monomeric subunits comprising a polymerized (meth)acrylate group and at least one alkoxyalkyl side group,
   wherein the co-monomer mixture has a First Ratio of the first monomeric subunit to the second and third monomeric subunits together from 1.2:1 to 3.5:1.

2. The composition of claim 1, wherein the aryloxy group of the second and/or third monomeric subunit comprises a phenoxy group and the aliphatic carbon moiety of the second and/or third monomeric subunit is substituted with at least one of a hydroxyl group or halogen.

3. The composition of claim 1, wherein the first monomeric subunit is about 40% to about 65%, by weight of the copolymer composition, and the second monomeric subunit is about 15% to about 30%, by weight of the copolymer composition, the third monomeric subunit is about 5% to about 30%, by weight of the copolymer composition, and the fourth monomeric subunit is about 5% to about 15%, by weight of the copolymer composition.

4. The composition of claim 1, wherein the alkylene oxide side group is a poly(alkylene oxide) side group.

5. The composition of claim 1, wherein the alkylene oxide side group has a molecular weight of 100 g/mol to 2,000 g/mol.

6. The composition of claim 1, wherein the alkylene oxide side group is a poly(ethylene oxide) side group.

7. The composition from claim 1, wherein the co-monomer mixture has a Second Ratio from 1.5:1 to 2.5:1 of the second monomeric subunit to the third monomeric subunit.

8. The composition of claim 1, wherein the first monomeric subunit consists of 2-ethoxyethoxyethyl methacrylate, the second monomeric subunit consists of 4-bromo-2-hydroxy-3-phenoxypropyl methacrylate, the third monomeric subunit consists of 2-hydroxy-3-phenoxypropyl methacrylate, and the fifth monomeric subunit comprises 2-ethoxyethyl.

9. The composition of claim 1, wherein the co-monomer mixture further includes a photo or thermal initiator.

10. The composition of claim 9, wherein the co-monomer mixture includes a photo initiator.

11. The composition of claim 1, wherein the co-monomer mixture further comprises a trimethacrylate crosslinker.

12. An intraocular lens comprising at least one copolymer consisting of:
   a 2-ethoxyethoxyethyl methacrylate first monomeric subunit;
   a 4-bromo-2-hydroxy-3-phenoxypropyl methacrylate second monomeric subunit;
   a 2-hydroxy-3-phenoxypropyl methacrylate third monomeric subunit;
   optionally a fourth monomeric subunit comprising an acrylate or (meth)acrylate group and at least one poly(alkyleneoxide) side group side group;
   optionally a fifth monomeric subunit comprising a polymerized (meth)acrylate group and at least one alkoxyalkyl side group;
   optionally one or more UV absorbing monomer;
   optionally one or more crosslinking agent; and
   optionally one or more photo and/or thermal initiator,
   wherein the co-monomer mixture has a ratio of the first monomeric subunit to the second and third monomeric subunits together from 1.2:1 to 3.5:1.

13. The intraocular lens of claim 12, wherein the 2-ethoxyethoxyethyl methacrylate monomeric subunit is about 50% to about 60% by weight of the monomeric subunits.

14. The intraocular lens of claim 12, wherein the 4-bromo-2-hydroxy-3-phenoxypropyl methacrylate monomeric subunit is about 20% to about 30% by weight of the monomeric subunits.

15. The intraocular lens of claim 12, wherein the fourth monomeric subunit is about 5% to 10% by weight of the monomeric subunits.

* * * * *